United States Patent [19]

Raddatz et al.

[11] Patent Number: 5,266,578
[45] Date of Patent: Nov. 30, 1993

[54] HETEROCYCLICALLY SUBSTITUTED QUINOLYLMETHOXY-PHENYLACETAMIDES

[75] Inventors: Siegfried Raddatz, Cologne; Klaus-Helmut Mohrs; Michael Matzke, both of Wuppertal; Romanis Fruchtmann, Cologne; Armin Hatzelmann, Konstanz; Christian Kohlsdorfer, Erftstadt; Reiner Müller-Peddinghaus, Bergisch-Gladbach; Pia Theisen-Popp, Aachen, all of Fed. Rep. of Germany

[73] Assignee: Bayer Aktiengesellschaft, Leverkusen, Fed. Rep. of Germany

[21] Appl. No.: 936,180

[22] Filed: Aug. 26, 1992

[30] Foreign Application Priority Data

Sep. 6, 1991 [DE] Fed. Rep. of Germany ........ 4129742

[51] Int. Cl.$^5$ ..................... A01N 43/42; C07C 215/38
[52] U.S. Cl. ..................................... 514/312; 514/314; 546/153; 546/155; 546/156; 546/157; 546/168; 546/175
[58] Field of Search ................ 541/175; 546/153, 155, 546/156, 157, 168; 514/312, 314

[56] References Cited

U.S. PATENT DOCUMENTS 5,041,453  8/1991  Huang et al. ........................ 546/175
5,102,881  4/1992  Zamboni et al. .................... 546/175

FOREIGN PATENT DOCUMENTS 0344519  5/1989  European Pat. Off. .
0399291  5/1990  European Pat. Off. .
87/05510 9/1987  PCT Int'l Appl. .

OTHER PUBLICATIONS

E. L. Eliel, Sterochemistry of Carbon Compounds, McGraw Hill, 1962 (whole book).
Th. Greene, "Protective Groups in Organic Synthesis," J. Wiley & Sons, 1981, New York.
John C. Sheehan, J. Am. Chem. Soc., 95, 1973, pp. 875-879.
Frank E. Frerman, J. Biological Chemistry, 1982, pp. 7087-7093.
N. Leo Benoiton, J. Peptide Protein Res. 17, 1981, pp. 197-204.
Henri Ulrich, J. Org. Chem., 1966, pp. 2658-2661.
Gunter E. Jeromin, Chem. Ber. 120, 1987, pp. 649-651.
Beilstein 22, p. 428 (1952).
Beilstein 27, p. 155. (1960).
Pierre Borgeat, Proc. Natl. Acad. Sci. USA, Jan. 30, 1979, pp. 2148-2152.

Primary Examiner—C. Warren Ivy
Assistant Examiner—Raymond Covington
Attorney, Agent, or Firm—Sprung Horn Kramer & Woods

[57] ABSTRACT

Heterocyclically substituted quinolylmethoxy-phenylacetamides are prepared by amidation of corresponding carboxylic acids. The compounds can be used in medicaments, in particular those having lipoxygenase-inhibiting action.

8 Claims, No Drawings

HETEROCYCLICALLY SUBSTITUTED QUINOLYLMETHOXY-PHENYLACETAMIDES

The invention relates to heterocyclically substituted quinolylmethoxy-phenylacetamides, to a process for their preparation and to their use in medicaments.

It has already been disclosed that quinolylmethoxy-phenylacylsulphonamides and -cyanamides have a lipoxygenase-inhibiting action [cf. EP 399,291]. 4-(quinolin-2-yl-methoxy)phenylacetic acid derivatives have additionally been disclosed in EP 344,519.

The present invention relates to heterocyclically substituted quinolylmethoxy-phenylacetamides of the general formula (I)

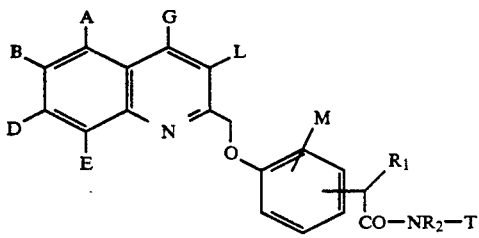

in which

A, B, D, E, G, L and M are identical or different and represent hydrogen, hydroxyl, halogen, cyano, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, $R^1$ represents straight-chain or branched alkyl having up to 10 carbon atoms, which is optionally substituted by aryl having 6 to 10 carbon atoms or by cycloalkyl having 3 to 8 carbon atoms, or represents cycloalkyl or -alkenyl having 3 to 12 carbon atoms, $R^2$ represents hydrogen or straight-chain or branched alkyl having up to 8 carbon atoms, T represents a saturated or unsaturated 5- to 7-membered heterocycle having up to 4 heteroatoms from the series comprising S, O and N, to which a saturated or unsaturated heterocycle or carbocycle is optionally fused, and which is optionally substituted by straight-chain or branched alkyl having up to 8 carbon atoms, halogen, benzyloxy or by a group of the formula —$NR^3R^4$ or —$SO_2R^5$, in which $R^3$ and $R^4$ are identical or different and denote hydrogen, phenyl, benzyl or straight-chain or branched alkyl having up to 8 carbon atoms and $R^5$ denotes cycloalkyl having 3 to 12 carbon atoms or aryl having 6 to 10 carbon atoms, which is optionally monosubstituted or disubstituted by identical or different halogen, cyano, hydroxyl, nitro, trifluoromethyl, trifluoromethoxy or trifluoromethylthio substituents, or by straight-chain or branched alkyl or alkoxy each having up to 8 carbon atoms, or denotes straight-chain or branched alkyl having up to 8 carbon atoms, which is optionally substituted by phenyl which in turn can be substituted by halogen, cyano, nitro, trifluoromethyl, trifluoromethoxy, trifluoromethylthio, hydroxyl or by straight-chain or branched alkyl or alkoxy each having up to 6 carbon atoms, and their salts.

Preferred 5- to 7-membered heterocycles are those substituted or unsubstituted by up to 4 heteroatoms from the series comprising S, N and O, to which a further heterocycle and/or a cyclohexyl, phenyl or naphthyl ring is optionally fused, such as, for example, naphthylpyridyl, 1,2,4-triazinyl, fluoranthrenyl, pyrazolopyrimidyl, imidazolyl, indolyl, isoquinolyl, isothiazolyl, tetrazolyl, thiazolyl, thiazolinyl, isoxazolyl, 1,2,4-triazolyl, 1,3,4-thiadiazolyl, benzimidazolyl, 2,1,3-benzothiadiazolyl, benzthiazolyl, pyridimidyl, quinolyl, benzoxazolyl, pyrazinyl, pyrryl, thienyl or furyl.

In the context of the present invention, physiologically acceptable salts are preferred. Physiologically acceptable salts of the quinolylmethoxy-phenylacetamides can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are additionally salts of metals, preferably univalent metals, and the ammonium salts. Preferred alkali metal salts are those such as sodium and potassium salts, and ammonium salts.

The compounds according to the invention exist in stereoisomeric forms which either behave as image and mirror image (enantiomers) or which do not behave as image and mirror image (diastereomers). The invention relates both to the antipodes and to the racemic forms and the diastereomer mixtures. Like the diastereomers, the racemic forms can be separated into the stereoisomerically uniform constituents in a known manner [cf. E. L. Eliel, Stereochemistry of Carbon Compounds, McGraw Hill, 1962].

Preferred compounds of the general formula (I) are those in which

A, B, D, E, G, L and M are identical or different and represent hydrogen, hydroxyl, fluorine, chlorine, bromine, carboxyl, nitro, trifluoromethyl, trifluoromethoxy or represent straight-chain or branched alkyl or alkoxy each having up to 6 carbon atoms, or represent phenyl which is optionally substituted by fluorine, chlorine, bromine, hydroxyl, nitro or cyano, $R^1$ represents straight-chain or branched alkyl having up to 8 carbon atoms, which is optionally substituted by phenyl, cyclopentyl, cyclohexyl or cycloheptyl, represents cyclobutyl, cyclopentyl, cyclohexyl, cycloheptyl or cyclooctyl, $R^2$ represents hydrogen or straight-chain or branched alkyl having up to 6 carbon atoms, T represents pyridyl, triazolyl, tetrazolyl, pyrryl, furyl, thienyl, thiazolyl, thiadiazolyl, thiazolinyl or imidazolyl each of which is optionally substituted by straight-chain or branched alkyl having up to 6 carbon atoms, fluorine, chlorine, bromine or by a group of the formula —$NR^3R^4$ OR —$SO_2R^5$, in which $R^3$ and $R^4$ are identical or different and denote hydrogen or straight-chain or branched alkyl having up to 6 carbon atoms and $R^5$ denotes cyclobutyl, cyclopentyl, cyclohexyl, cycloheptyl, cyclooctyl or phenyl, which is optionally substituted by fluorine, chlorine, bromine, iodine, cyano or by a straight-chain or branched alkyl or alkoxy each having up to 6 carbon atoms, or denotes straight-chain or branched alkyl having up to 6 carbon atoms, which is optionally substituted by phenyl which in turn can be substituted by fluorine, chlorine, bromine, trifluoromethyl or by straight-chain or branched alkyl or alkoxy each having up to 4 carbon atoms, and their salts.

Particularly preferred compounds of the general formula (I) are those
in which

A, B, D, E, G, L and M are identical or different and represent hydrogen, hydroxyl, fluorine, chlorine, bromine or straight-chain or branched alkyl having up to 4 carbon atoms, $R^1$ represents straight-chain or branched alkyl having up to 6 carbon atoms, which is optionally substituted by phenyl or cyclohexyl, represents cyclobutyl, cyclopentyl, cyclohexyl, cycloheptyl or cyclooctyl, $R^2$ represents hydrogen or straight-chain or branched alkyl having up to 4 carbon atoms, T represents pyridyl, triazolyl, tetrazolyl, thiazolyl, thiadiazolyl or thiazolinyl, each of which is optionally substituted by straight-chain or branched alkyl having up to 4 carbon atoms, fluorine, chlorine, amino or by a group of the formula $-SO_2R^5$,
in which $R^5$ denotes cyclopentyl, cyclohexyl, cycloheptyl, cyclooctyl or phenyl, which is optionally substituted by fluorine, chlorine, bromine, iodine, methoxy or trifluoromethyl, or denotes straight-chain or branched alkyl having up to 4 carbon atoms, which is optionally substituted by phenyl which in turn can be substituted by fluorine, chlorine, bromine, methyl or methoxy, and their salts.

Very particularly preferred compounds of the formula (I) are those in which A, B, D, E, G, L and M represent hydrogen. Moreover, those compounds are very particularly preferred in which the group —CH-$R^1$—$CO$—$NR^2$—T is in the 4-position to the quinolylmethoxy radical.

A process for the preparation of the compounds of the general formula (I) according to the invention has additionally been found, characterised in that
compounds of the general formula (II)

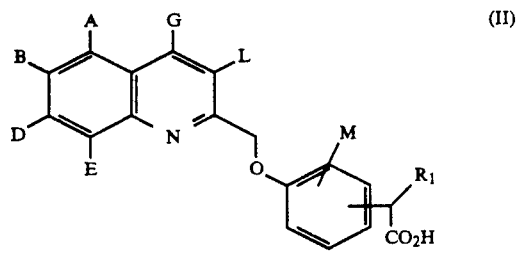

in which

A, B, D, E, G, L, M and $R^1$ have the abovementioned meaning, are amidated with compounds of the general formula (III)

$$H_2N-T \qquad (III)$$

in which

T has the abovementioned meaning, in inert solvents in the presence of a base and/or of an auxiliary and optionally with activation of the carboxylic acid function, and in the case of the enantiomers, the corresponding enantiomerically pure acids (II) are previously separated, where the substituents A, B, D, E, G, L, M and $R^1$ can optionally be varied according to customary methods.

The process according to the invention can be illustrated by way of example by the following equation:

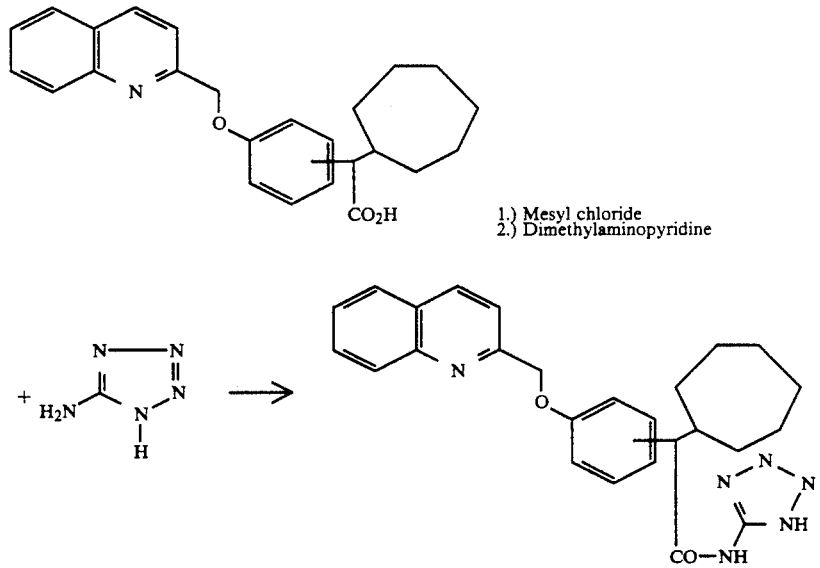

1.) Mesyl chloride
2.) Dimethylaminopyridine

The amidation is in general carrie dout in inert solvents in the presenc eof a base and of a dehydrating agent.

Suitable solvents for th eprocess according to the invention are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetates, or triethylamine, pyridine, dimethyl sulphoxide, dimethylformamide, hexamethylphosphoric triamide, acetonitrile, acetone or nitromethane. It is also possible to use mixtures of the solvents mentioned. Tetrahydrofuran is preferred.

Suitable bases for the process according to the invention are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alkoxides such as, for example, sodium methoxide or ethoxide, potassium methoxide or ethoxide or potassium tert-butoxide, or organic amines such as benzyltrimethylammonium hydroxide, tetrabutylammonium hydroxide, pyridine, 2-dimethylaminopyridine, triethylamine or N-methylpiperidine. Triethylamine and dimethylaminopyridine are preferred.

When carrying out the amidation, the base is in general employed in an amount from 1 to 3 mol, preferably from 1 to 1.5 mol, relative to 1 mol of the carboxylic acid (II).

The amidation is in general carried out at normal pressure. However, it is also possible to carry out the process at reduced pressure or at elevated pressure (for example in a range from 0.5 to 5 bar).

The amidation is in general carried out in a temperature range from 0° C. to 150° C., preferably at 25° C. to 40° C.

The auxiliaries employed are in general dehydrating agents, such as are known from the literature of peptide chemistry.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxytris-(dimethylamino)phosphonium hexafluorophosphate or diphenyl phosphoramidate or methanesulphonyl chloride, if appropriate in the presence of bases such as triethylamine, dimethylaminopyridine or N-ethylmorpholine or N-methylpiperidine or dicyclohexylcarbodiimide and N-hydroxysuccinimide [cf. J.C. Sheehan, S. L. Edis, J. Am. Chem. Soc. 95, 875 (1973); F.E. Freeman et al., J. Biol. Chem. 225, 507 (1982) and N.B. Benoiton and K. Kuroda, Int. Pept Prot. Res. 13, 403 (1979), (1981)].

The compounds of the general formula (II) are largely known [cf. for example EP 399,291; EP 181,568]or can be prepared according to a customary method, by first etherifying compounds of the general formula (IV)

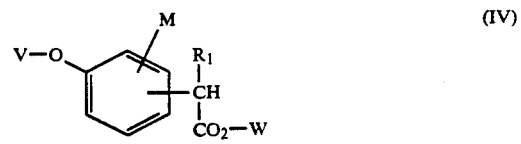

in which

R$^1$ has the above mentioned meaning,

V represents a customary hydroxyl protective group, preferably benzyl or tert-butyl and W represents a $C_1$-$C_6$-alkyl radical, after removal of the protective group V, with 2-halogenomethylquinolines of the general formula (V)

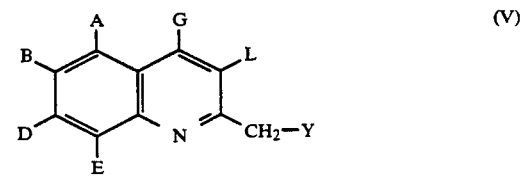

in which

A, B, D, E, G and L have the abovementioned meaning and

Y represents halogen, in particular chlorine or bromine, in inert solvents and then hydrolysing, it also being possible at any time to vary the substituents A, B, D, E, G, L and M according to a customary method at the stages of the general formula (IV) and (V).

The removal of the protective groups from the corresponding ethers (IV) is carried out according to a customary method, for example by hydrogenolytic cleavage of the benzyl ethers in the abovementioned inert solvents in the presence of a catalyst with hydrogen gas [cf. additionally Th. Greene: "Protective Groups in Organic Synthesis", J. Wiley & Sons, 1981, New York].

The etherification can be carried out in inert organic solvents, if appropriate in the presence of a base. Solvents for the etherification can be inert organic solvents which do not change under the reaction conditions. These preferably include ethers such as, for example, dioxane, tetrahydrofan or diethyl ether, halogenohydrocarbons such as dichloromethane, trichloromethane, tetrachloromethane, 1,2-dichloroethane or trichloroethylene, hydrocarbons such as benzene, xylene, toluene, hexane, cyclohexane or mineral oil fractions, nitromethane, dimethylformamide, acetonitrile, acetone or hexamethylphosphoric triamide. It is also possible to employ mixtures of the solvents.

Bases employed for the etherification can be inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl($C_1$-$C_6$) amines) such as triethylamine, or heterocycles such as pyridine, methylpiperidine, piperidine or morpholine.

It is also possible to employ as bases alkali metals such as sodium and its hydrides, such as sodium hydride.

The etherification is in general carried out in a temperature range from 0° C. to +150° C., preferably from 10° C. to +100° C.

The etherification is in general carried out at normal pressure. However, it is also possible to carry out the process at reduced pressure or elevated pressure (for example in a range from 0.5 to 5 bar).

In general, 0.5 to 5 mol, preferably 1 to 2 mol, of halide (V) are employed relative to 1 mol of the reaction component. The base is in general employed in an amount from 0.5 to 5 mol, preferably from 1 to 3 mol, relative to the halide.

The compounds of the general formula (IV) are known per se or can be prepared according to a customary method [cf. J. Org. Chem. 31, 2658 (1966)].

The compounds of the general formula (V) and their preparation are also known [cf. Chem. Ber. 120, 649 (1987).

The hydrolysis of the carboxylic acid esters is carried out according to customary methods by treating the esters in inert solvents with customary bases.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkaline metal carbonates such as sodium carbonate or potassium carbonate or sodium hydrogen carbonate. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to use mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The heterocyclic amines of the general formula (III) are known or can be prepared according to a customary method [cf. for example Beilstein 22, 428; Beilstein 27, 155].

The heterocyclic quinolylmethoxy-phenylacetamides according to the invention can be employed as active substances in medicaments. The substances can act as inhibitors of enzymatic reactions in the context of arachidonic acid metabolism, in particular of lipoxygenase.

They are thus preferably suitable for the treatment and prevention of disorders of the airways such as allergies/asthma, bronchitis, emphysema, shock lung, pulmonary hypertension, inflammations/rheumatism and oedemas, thromboses and thromboembolisms, ischemias (peripheral, cardiac and cerebral circulatory disorders), cardiac and cerebral infarcts, angina pectoris, arteriosclerosis, in tissue transplants, dermatoses such as psoriasis, inflammatory dermatoses and for cytoprotection in the gastrointestinal tract.

The heterocyclic quinolylmethoxy-phenylacetamides according to the invention can be used both in human medicine and in veterinary medicine.

The pharmacological effects of the substances according to the invention are determined by the following method:

As a measure of the lipoxygenase inhibition, the release of leukotriene $B_4$ (LTB.) in polymorphonuclear human leukocytes (PMN) was determined by addition of substances and Ca ionophore by means of reverse phase HPLC according to Borgeat, P. et al., Proc. Nat. Acad. Sci, 76, 2148–2152 (1979).

Table 1 lists by way of example the values obtained by this test for some compounds according to the invention:

TABLE 1

| Example No. | 5-LO $IC_{50}$ ($\mu$mol/l) |
|---|---|
| 1 | $5 \times 10^{-7}$ |
| 2 | $2.6 \times 10^{-7}$ |
| 3 | $2.9 \times 10^{-7}$ |
| 4 | $4.3 \times 10^{-7}$ |

The present invention also includes pharmaceutical preparations which, in addition to inert, non-toxic, pharmaceutically suitable auxiliaries and excipients, contain one or more compounds of the general formula (I), or which consist of one or more active substances of the formula (I), and processes for the production of these preparations.

The active substances of the formula (I) should be present in these preparations in a concentration of 0.1 to 99.5% by weight, preferably of 0.5 to 95% by weight of the total mixture.

In addition to the active substances of the formula (I), the pharmaceutical preparations can also contain other pharmaceutical active substances.

The abovementioned pharmaceutical preparations can be prepared in a customary manner by known methods, for example with the auxiliary(ies) or excipient(s).

In general, it has proved advantageous to administer the active substance(s) of the formula (I) in total amounts of about 0.01 to about 100 mg/kg, preferably in total amounts of about 1 mg/kg to 50 mg/kg of body weight every 24 hours, if appropriate in the form of several individual doses, to achieve the desired result.

However, it may be advantageous to depart from the amounts mentioned, in particular depending on the nature and on the body weight of the subject to be treated, on individual behaviour towards the medicament, the nature and severity of the disorder, the type of preparation and administration, and the time or interval at which administration takes place.

STARTING COMPOUNTS

Example I

2-[4-(Quinolin-2-yl-methoxy)phenyl]-2-cycloheptylacetic acid

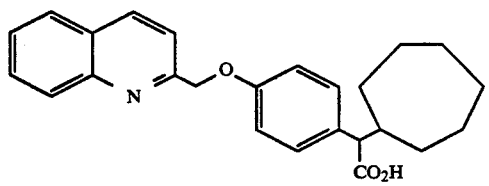

11 g (27 mmol) of methyl 2-[4-(quinolin-2-yl-methoxy)-phenyl]-2-cycloheptyl acetate in 200 ml 55.4 ml of 1 molar sodium hydroxide solution are heated to reflux for 10 h. After cooling, the mixture is acidified with concentrated hydrochloric acid, and the precipitated product is filtered off with suction and dried.

Yield: 9.3 g (87% of theory)
Solidification point: 176° C.

PREPARATION EXAMPLES

Example 1

N-(2-Pyridyl)-2-[4-(quinolin-2-yl-methoxy)phenyl]-2-cycloheptyl-acetamide

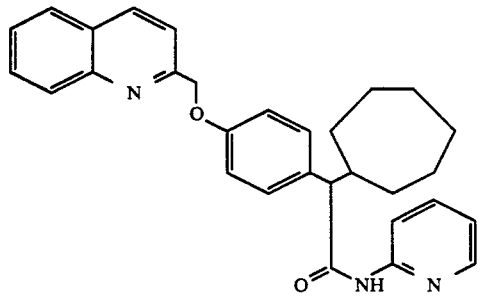

2 g (0.005 mol) of the compound from Example I are suspended at room temperature in 20 ml of dried THF, cooled under argon to 0° C. in an ice-bath and treated with stirring with 1.4 ml =1.0 g (0.01 mol) of triethylamine. A clear solution is formed during the course of this. After addition of 0.39 ml 0.58 g (0.005 mol) of methanesulphonyl chloride at 0° C., the mixture is stirred in an ice-bath for 2 h. Colourless crystals are obtained in this way. 0.56 g (0.006 mol) of 2-aminopyridine and 1.2 g (0.01 mol) of dimethylaminopyridine, dissolved in 10 ml of dry THF, are added with stirring to this mixture. The suspension is initially coloured yellow, but later becomes colourless again. The mixture is stirred overnight at room temperature. After addition of 2 ml of 2 N acetic acid, the whole is evaporated to dryness in vacuo. The residue is taken up in 70 ml of tolulene, extracted by shaking with satd. NaHOC$_3$ solution and water, the organic phase is dried with sodium sulphate and concentrated to a small volume, and the residue is separated by column chromatography (silica gel 60, eluent: dichloromethane: ethyl acetate: acetic acid =80:10:10).

Yield : 2.7 g (75.3% of theory) of colourless crystals
M.p.: 137° C.

Example 2

N-(5-Tetrazolyl)-2-[4-(quinoline-2-yl-methoxy)-phenyl]-2-cycloheptyl-acetamide

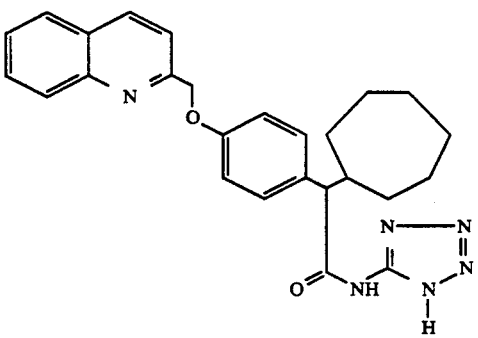

2 g (0.005 mol) of the compound from Example I and 2 ml =1.5 g (0.015 mol) of triethylamine are dissolved in 30 ml of THF, cooled to 0° C., and then treated dropwise with 0.8 ml=1.1 g (0.01 mol) of mesyl chloride, and 1.2 g (0.01 mol) of dimethylaminopyridine and 0.6 g (0.006 mol) of 5-aminotetrazole are then added. The whole is stirred overnight at room temperature and concentrated to dryness in vacuo, and the residue is stirred with 10 ml of water. The filtered-off and dried residue is dissolved in a little ethyl acetate and separated by column chromatography (silica gel 60, eluent: toluene, ethyl acetate, glacial acetic acid =8,1,1).

Yield: 1.8 g (79% of theory) of colourless crystals
M.p.: about 255° C. (dec.)

Example 3

N-(2-Thiazolinyl)-2-[4-(quinolin-2-yl-methoxy)-phenyl]-2-cycloheptyl-acetamide

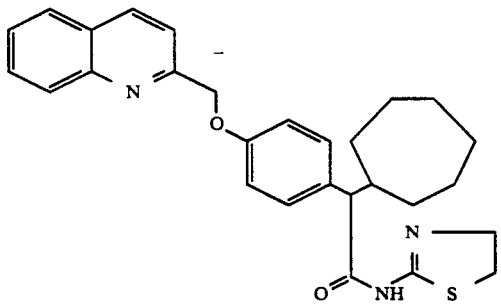

2.0 g (0.005 mol) of the compound from Example I and 1.4 ml=1.0 g (0.01 mol) of triethylamine are dissolved in 30 ml of THF, and the solution is cooled to 0° C., treated dropwise with 0.4 ml=0.6 g (0.0052 mol) of mesyl chloride and then with 0.6 g (0.006 mol) of 2-aminothiazoline and 1.2 g (0.01 mol) of dimethylaminopyridine in 15 ml of THF. The mixture is stirred overnight at room temperature. The solvent is then evaporated to dryness in vacuo, the residue is taken up in 50 ml of dichloromethane and the solution is extracted twice by shaking with 15 ml of water. After drying with sodium sulphate and concentrating to a small volume, the mixture is separated by column chromatography (silica gel 60, eluent: toluene, ethyl acetate, glacial acetic acid =8/1/1).

Yield: 1.0 g (42% of theory) of colourless foam
M.p.: about 80° C.

Example 4

N-(2-Thiazolyl)-2-[4-(quinolin-2-yl-methoxy)-phenyl]-2-cycloheptyl-acetamide

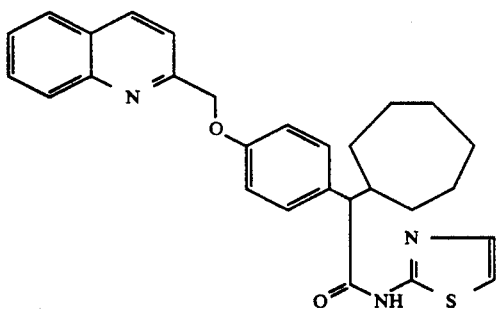

In analogy to the procedure of Example 3, 2.0 g (0.005 mol) of the compound from Example I, 1.4 ml=1.0 g (0.01 mol) of triethylamine, 0.4 ml=0.6 g (0.0052 mol) of mesyl chloride, 0.6 g (0.006 mol) of 2-aminothiazole and 1.2 g (0.01 mol) of dimethylaminopyridine are reacted to prepare the title compound.

Yield: 1.8 g (77% of theory) of colourless crystals
M.p.: 166° C.

Examole 5

N-(5-Cyclohexylsulphonyl-1,3,4-thiadiazolyl-2-yl)-2-[4-(quinolin-2-yl-methoxy)-phenyl] -2-cyclohepthyacetamide

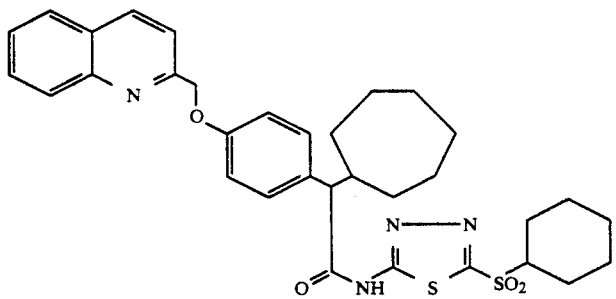

In analogy to the procedure of Example 3, the title compound is prepared from 1.5 g (0.0039 mol) of the compound from Example I, 1.05 ml=0.75 g (0.0089 mol) of triethylamine, 0.3 ml=0.45 g (0.004 mol) of mesyl chloride, 0.96 g (0.004 mol) of 2-amino-5-cyclohexylsulphonyl-1,3,4-thiadiazole and 0.9 g (0.0075 mol) of dimethylaminopyridine.

Yield: 0.9 g (37.8% of theory) of colourless crystals
M.p.: 183° C.

What we claim is:

1. Heterocyclicallysubstitutedquinolylmethoxyphenylacetamides of the general formula

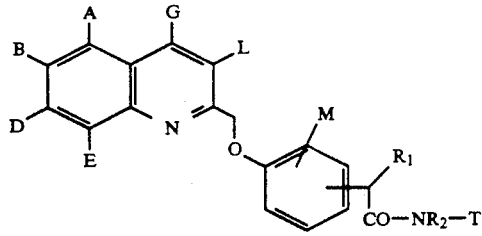

in which

A, B, D, E, G, L and M are identical or different and represent hydrogen, hydroxyl, halogen, cyano, carboxyl, nitro, trifluoromethyl, trifluoromethoxy or represent straight-chain or branched alkyl or alkoxy each having up to 8 carbon atoms, or represent aryl having 6 to 10 carbon atoms, which is optionally substituted by halogen, hydroxyl, nitro or cyano, $R^1$ represents straight-chain or branched alkyl having up to 10 carbon atoms, which is optionally substituted by aryl having 6 to 10 carbon atoms or by cycloalkyl having 3 to 8 carbon atoms, or represents cycloalkyl or -alkenyl having 3 to 12 carbon atoms, $R^2$ represents hydrogen or straight-chain or branched alkyl having up to 8 carbon atoms, T represents a saturated or unsaturated 5 to 7 membered heterocycle having up to 4 heteroatoms from the series comprising S, O and N, to which a saturated or unsaturated heterocycle or carbocycle is optionally fused, and which is optionally substituted by straight-chain or branched alkyl having up to 8 carbon atoms, halogen, benzyloxy or by a group of the formula —$NR^3R^4$ or —$SO_2R^5$, in which $R^3$ and $R^4$ are identical or different and denote hydrogen, phenyl, benzyl or straightchain or branched alkyl having up to 8 carbon atoms and $R^5$ denotes cycloalkyl having 3 to 12 carbon atoms or aryl having 6 to 10 carbon atoms, which is optionally monosubstituted or disubstituted by identical or different halogen, cyano, hydroxyl, nitro, trifluoromethyl, trifluoromethoxy or trifluoromethylthio substituents, or by straight-chain or branched alkyl or alkoxy each having up to 8 carbon atoms, or denotes straight-chain or branched alkyl having up to 8 carbon atoms, which is optionally substituted by phenyl which in turn can be substituted by halogen, cyano, nitro, trifluoromethyl, trifluoromethoxy, trifluoromethylthio, hydroxyl or by straight-chain or branched alkyl or alkoxy each having up to 6 carbon atoms, and their salts.

2. Heterocyclicallysubstituted quinolylmethoxyphenylacetamides according to Claim 1, in which A, B, D, E, G, L and M are identical or different and represent hydrogen, hydroxyl, fluorine, chlorine, bromine, carboxyl, nitro, trifluoromethyl, trifluoromethoxy or represent straight-chain or branched alkyl or alkoxy each having up to 6 carbon atoms, or represent phenyl which is optionally substituted by fluorine, chlorine, bromine, hydroxyl, nitro or cyano, $R^1$ represents straight-chain or branched alkyl having up to 8 carbon atoms, which is optionally substituted by phenyl, cyclopentyl, cyclohexyl or cycloheptyl, represents cyclobutyl, cyclopentyl, cyclohexyl, cycloheptyl or cyclooctyl, $R^2$ represents hydrogen or straight-chain or branched alkyl having up to 6 carbon atoms, T represents pyridyl, triazolyl, tetrazolyl, pyrryl, furyl, thienyl, thiazolyl, thiadiazolyl, thiazolinyl or imidazolyl each of which is optionally substituted by straight-chain or branched alkyl having up to 6 carbon atoms, fluorine, chlorine, bromine or by a group of the formula $-NR^3R^4$ OR $-SO_2R^5$, in which $R^3$ and $R^4$ are identical or different and denote hydrogen or straight-chain or branched alkyl having up to 6 carbon atoms and $R^5$ denotes cyclobutyl, cyclopentyl, cyclohexyl, cycloheptyl, cyclooctyl or phenyl, which is optionally substituted by fluorine, chlorine, bromine, iodine, cyano or by a straight-chain or branched alkyl or alkoxy each having up to 6 carbon atoms, or denotes straight-chain or branched alkyl having up to 6 carbon atoms, which is optionally substituted by phenyl which in turn can be substituted by fluorine, chlorine, bromine, trifluoromethyl or by straight-chain or branched alkyl or alkoxy each having up to 4 carbon atoms, and their salts.

3. Heterocyclicallysubstitutedquinolylmethoxyphenylacetamides according to Claim 1, in which A, B, D, E, G, L and M are identical or different and represent hydrogen, hydroxyl, fluorine, chlorine, bromine or straight-chain or branched alkyl having up to 4 carbon atoms, $R^1$ represents straight-chain or branched alkyl having up to 6 carbon atoms, which is optionally substituted by phenyl or cyclohexyl, represents cyclobutyl, cyclopentyl, cyclohexyl, cycloheptyl or cyclooctyl, $R^2$ represents hydrogen or straight-chain or branched alkyl having up to 4 carbon atoms, T represents pyridyl, triazolyl, tetrazolyl, thiazolyl, thiadiazolyl or thiazolinyl, each of which is optionally substituted by straight-chain or branched alkyl having up to 4 carbon atoms, fluorine, chlorine, amino or by a group of the formula $-SO_2R^5$, in which $R^5$ denotes cyclopentyl, cyclohexyl, cycloheptyl, cyclooctyl or phenyl, which is optionally substituted by fluorine, chlorine, bromine, iodine, methoxy or trifluoromethyl, or denotes straight-chain or branched alkyl having up to 4 carbon atoms, which is optionally substituted by phenyl which in turn can be substituted by fluorine, chlorine, bromine, methyl or methoxy, and their salts 4. Heterocyclically substituted quinolylmethoxyphenylacetamides according to Claim 1, in which the group $-CHR^1-CO-NR^2-T$ is in the 4-position to the quinolylmethoxy radical.

5. A compound according to claim 1 wherein such compound is N-(5-tetrazolyl)-2-[4-(quinoline-2-ylmethoxy)phenyl]-2-cycloheptyl-acetamide of the formula

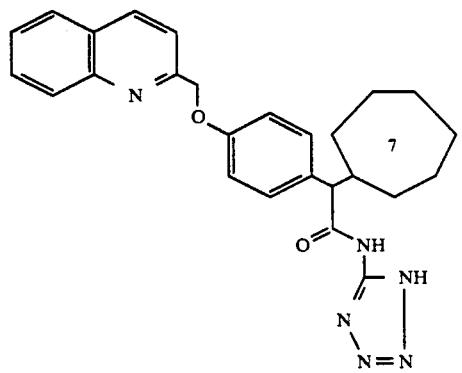

and a salt thereof.

6. A compound according to claim wherein such compound is N-(2-thiazolyl)-2-[4-(quinoline-2-ylmethoxy)phenyl]-2-cycloheptyl-acetamide of the formula

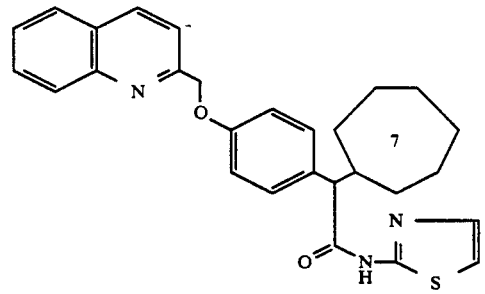

and a salt thereof.

7. A composition for the inhibition of enzymatic reactions in the context of arachidonic acid metabolism comprising an amount effective therefor of a compound or salt thereof according to claim 1 and a pharmacologically acceptable diluent.

8. The method of inhibiting the enzymatic reactions in the context of arachidonic acid metabolism in a patient in need thereof which comprises administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,266,578
DATED : November 30, 1993
INVENTOR(S) : Raddatz, et al.

It is certified that error appears in the above-indentified patent and that said Letters Patent is hereby corrected as shown below:

Col. 12, lines 28-   After represents " delete " a saturated or unsaturated 5 to 7 membered heterocycle having up to 4 heteroatoms from the series comprising S, O and N, to which a saturated or unsaturated heterocycle or carbocycle is optionally fused " and substitute -- pyridyl, triazolyl, tetrazoyl, pyrryl, furyl, thienyl, thiazolyl, thiadiazolyl, thiazolinyl or imidazolyl, each of --

Col. 14, line 36    After " claim " insert -- 1 --

Signed and Sealed this

Fifth Day of September, 1995

Attest:

BRUCE LEHMAN

Attesting Officer

Commissioner of Patents and Trademarks